(12) United States Patent
Smith et al.

(10) Patent No.: US 12,280,214 B2
(45) Date of Patent: Apr. 22, 2025

(54) CONDUIT WITH HEATING ELEMENT

(71) Applicant: Fisher & Paykel Healthcare Limited, Auckland (NZ)

(72) Inventors: Daniel John Smith, Auckland (NZ); David Peter Baldwin, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 900 days.

(21) Appl. No.: 17/178,579

(22) Filed: Feb. 18, 2021

(65) Prior Publication Data

US 2021/0275770 A1 Sep. 9, 2021

Related U.S. Application Data

(63) Continuation of application No. 15/789,827, filed on Oct. 20, 2017, now Pat. No. 10,953,184, which is a continuation of application No. 13/272,047, filed on Oct. 12, 2011, now Pat. No. 9,827,393, which is a continuation of application No. 10/684,917, filed on Oct. 14, 2003, now Pat. No. 8,037,882.

(51) Int. Cl.
| | |
|---|---|
| *A61M 16/00* | (2006.01) |
| *A61M 16/08* | (2006.01) |
| *A61M 16/10* | (2006.01) |

(52) U.S. Cl.
CPC ........ *A61M 16/1075* (2013.01); *A61M 16/08* (2013.01); *A61M 16/0816* (2013.01); *A61M 16/0833* (2014.02); *A61M 16/0883* (2014.02); *A61M 16/1045* (2013.01); *A61M 16/1095* (2014.02)

(58) Field of Classification Search
CPC .. A61M 16/00; A61M 15/1075; A61M 16/08; A61M 16/0833; A61M 16/1095; A61M 16/0816; A61M 16/1045; F28F 13/18; F28F 13/02
See application file for complete search history.

(56) References Cited

U.S. PATENT DOCUMENTS

| 928,237 A | 7/1909 | Baird |
|---|---|---|
| 1,361,206 A | 12/1920 | Verhunce |
| (Continued) | | |

FOREIGN PATENT DOCUMENTS

| AU | 1947468122 | 4/1974 |
|---|---|---|
| AU | 1352900 | 6/2000 |
| (Continued) | | |

OTHER PUBLICATIONS

U.S. Appl. No. 09/850,797, filed May 8, 2001, Smith et al.
(Continued)

*Primary Examiner* — Margaret M Luarca
*Assistant Examiner* — Sarah B Lederer
(74) *Attorney, Agent, or Firm* — VIA LLP

(57) ABSTRACT

A conduit for a breathing circuit includes a heater associated, at least in part, with a hydrophilic layer. The purpose of the heater is to evaporate any condensed liquid collecting in the conduit, which is first sucked up by the hydrophilic layer. The heated wick reduces the risk of collected water being passed to the patient and causing choking fits or discomfit. It is preferred that the heated wick lies freely in the conduit to settle at low points in the conduit where condensation may collect.

14 Claims, 7 Drawing Sheets

(56) References Cited

U.S. PATENT DOCUMENTS

| | | | |
|---|---|---|---|
| 1,406,578 | A | 2/1922 | Murray |
| 1,558,804 | A | 10/1925 | Greenwald |
| 2,250,430 | A | 7/1941 | Wade |
| 2,748,830 | A | 6/1956 | Nash et al. |
| 2,868,199 | A | 1/1959 | Hudson |
| 2,917,568 | A | 12/1959 | Moorman et al. |
| 2,943,644 | A | 7/1960 | Moseley |
| 3,144,313 | A | 8/1964 | Pfefferie |
| 3,163,707 | A | 12/1964 | Darling |
| 3,188,117 | A | 6/1965 | Press et al. |
| 3,228,877 | A | 1/1966 | Mahon |
| 3,245,206 | A | 4/1966 | Bonnet |
| 3,271,221 | A | 9/1966 | Sheehan |
| 3,279,333 | A | 10/1966 | Blair et al. |
| 3,292,346 | A | 12/1966 | Adams |
| 3,294,609 | A | 12/1966 | Foll |
| 3,303,105 | A | 2/1967 | Konikoff et al. |
| 3,307,330 | A | 3/1967 | Niedzielski et al. |
| 3,307,589 | A | 3/1967 | Sheffield |
| 3,349,806 | A | 10/1967 | Roberts |
| 3,367,850 | A | 2/1968 | Johnson |
| 3,376,181 | A | 4/1968 | Larson et al. |
| 3,394,954 | A | 7/1968 | Sarns |
| 3,434,471 | A | 3/1969 | Liston |
| 3,513,844 | A | 5/1970 | Smith |
| 3,578,777 | A | 5/1971 | Degain |
| 3,616,796 | A | 11/1971 | Jackson |
| 3,639,970 | A | 2/1972 | Larkin |
| 3,677,329 | A | 7/1972 | Kirkpatricks |
| 3,682,171 | A | 8/1972 | Dali et al. |
| 3,693,856 | A | 9/1972 | Funk |
| 3,700,513 | A | 10/1972 | Haberhauer et al. |
| 3,735,558 | A | 5/1973 | Skarstrom et al. |
| 3,735,559 | A | 5/1973 | Salemme |
| 3,739,815 | A | 6/1973 | Rajeski |
| 3,754,552 | A | 8/1973 | King |
| 3,773,447 | A | 11/1973 | Barratt |
| 3,803,810 | A | 4/1974 | Rosenberg |
| 3,829,340 | A | 8/1974 | Dembiak et al. |
| 3,834,257 | A | 9/1974 | Ganser |
| 3,856,051 | A | 12/1974 | Bain |
| 3,857,415 | A | 12/1974 | Morin et al. |
| 3,866,632 | A | 2/1975 | Schaffer |
| 3,871,373 | A | 3/1975 | Jackson |
| 3,889,717 | A | 6/1975 | Obadal et al. |
| 3,891,556 | A | 6/1975 | Ricahrdson et al. |
| 3,895,630 | A | 7/1975 | Bachman |
| 3,910,808 | A | 10/1975 | Steward |
| 3,911,962 | A | 10/1975 | Chomat et al. |
| 3,912,795 | A | 10/1975 | Jackson |
| 3,945,867 | A | 3/1976 | Steward |
| 3,963,856 | A | 6/1976 | Carlson et al. |
| 3,966,525 | A | 6/1976 | Steward |
| 4,000,759 | A | 1/1977 | Higbee |
| 4,007,737 | A | 2/1977 | Paluch |
| 4,035,211 | A | 7/1977 | Bill et al. |
| 4,048,993 | A | 9/1977 | Dobritz |
| 4,083,245 | A | 4/1978 | Osborn |
| 4,086,035 | A | 4/1978 | Klaeger, Jr. et al. |
| 4,130,617 | A | 12/1978 | Wallace |
| 4,180,103 | A | 12/1979 | Mollere |
| 4,204,562 | A | 5/1980 | Kelly |
| 4,207,457 | A | 6/1980 | Haglunc et al. |
| 4,216,769 | A | 8/1980 | Grimes |
| 4,229,613 | A | 10/1980 | Braum |
| 4,262,704 | A | 4/1981 | Grawey |
| 4,265,235 | A | 5/1981 | Fukunaga |
| 4,265,239 | A | 5/1981 | Fischer, Jr. |
| 4,295,496 | A | 10/1981 | Bixby |
| 4,304,266 | A | 12/1981 | Kutnyak et al. |
| 4,318,398 | A | 3/1982 | Oetjen et al. |
| 4,327,718 | A | 5/1982 | Cronenberg |
| 4,327,775 | A | 5/1982 | Tally |
| 4,336,798 | A | 6/1982 | Beran |
| 4,337,800 | A | 7/1982 | Carlson et al. |
| 4,343,672 | A | 8/1982 | Kanao |
| 4,359,086 | A * | 11/1982 | Sanborn ............... F28F 13/187 165/907 |
| 4,367,735 | A | 1/1983 | Dali |
| 4,368,088 | A | 1/1983 | Asakura et al. |
| 4,381,210 | A | 4/1983 | Isizuka et al. |
| 4,403,514 | A | 9/1983 | Osborn |
| 4,406,283 | A | 9/1983 | Bir |
| 4,406,514 | A | 9/1983 | Hillegonds et al. |
| 4,415,389 | A | 11/1983 | Medford et al. |
| 4,417,574 | A | 11/1983 | Talonn et al. |
| 4,420,016 | A | 12/1983 | Nichols |
| 4,430,603 | A | 2/1984 | Muller |
| 4,456,034 | A | 6/1984 | Bixby |
| 4,462,397 | A | 7/1984 | Suzuki |
| 4,463,755 | A | 8/1984 | Suzuki |
| 4,469,495 | A | 9/1984 | Hiraizumi et al. |
| 4,488,921 | A | 12/1984 | Dougherty |
| 4,490,575 | A | 12/1984 | Kutnyak |
| 4,493,870 | A | 1/1985 | Vrouenraets et al. |
| 4,509,359 | A | 4/1985 | Gedeon et al. |
| 4,517,404 | A | 5/1985 | Hughes et al. |
| 4,580,816 | A | 4/1986 | Campbell et al. |
| 4,592,351 | A | 6/1986 | Smith et al. |
| 4,597,596 | A | 7/1986 | Tozer |
| 4,606,380 | A | 8/1986 | Jartoux |
| 4,621,632 | A | 11/1986 | Bartels et al. |
| 4,653,542 | A | 3/1987 | Tascher |
| 4,669,508 | A | 6/1987 | Neaves |
| 4,682,010 | A | 7/1987 | Drapeau et al. |
| 4,686,354 | A | 8/1987 | Makin |
| 4,698,196 | A | 10/1987 | Fabian |
| 4,698,890 | A | 10/1987 | Neaves |
| 4,705,543 | A | 11/1987 | Kertzman |
| 4,708,831 | A | 11/1987 | Elsworth et al. |
| 4,715,915 | A | 12/1987 | Vanderzee |
| 4,722,334 | A | 2/1988 | Blackmer et al. |
| 4,753,233 | A | 6/1988 | Grimes |
| 4,758,397 | A | 7/1988 | Schreiner et al. |
| 4,771,770 | A | 9/1988 | Artemenko et al. |
| 4,773,410 | A | 9/1988 | Blackmer et al. |
| 4,791,963 | A | 12/1988 | Gronert et al. |
| 4,808,201 | A | 2/1989 | Kertzman |
| 4,825,863 | A | 5/1989 | Dittmar et al. |
| 4,838,258 | A | 6/1989 | Kertzman |
| 4,844,719 | A | 7/1989 | Toyomoto et al. |
| 4,854,416 | A | 8/1989 | Lalikos et al. |
| 4,874,925 | A | 10/1989 | Dickenson |
| 4,875,908 | A | 10/1989 | Kikukawa et al. |
| 4,886,528 | A | 12/1989 | Aaltonen et al. |
| 4,900,596 | A | 2/1990 | Peacock |
| 4,910,384 | A | 3/1990 | Silver |
| 4,915,104 | A | 4/1990 | Marcy |
| 4,915,105 | A | 4/1990 | Lee |
| 4,919,128 | A | 4/1990 | Kopala et al. |
| 4,932,269 | A | 6/1990 | Cammarata, III et al. |
| 4,938,752 | A | 7/1990 | Vrouenraets et al. |
| 4,942,905 | A | 7/1990 | Takemae et al. |
| 4,967,744 | A | 11/1990 | Chua |
| 4,985,055 | A | 1/1991 | Thorne et al. |
| 4,995,384 | A | 2/1991 | Keeling |
| 5,042,500 | A | 8/1991 | Norlien et al. |
| 5,044,361 | A | 9/1991 | Werner et al. |
| 5,046,531 | A | 9/1991 | Kanao |
| 5,062,145 | A | 10/1991 | Zwaan et al. |
| 5,088,332 | A | 2/1992 | Merilainen et al. |
| 5,121,746 | A | 6/1992 | Silora |
| 5,160,511 | A | 11/1992 | Lovelock |
| 5,165,395 | A | 11/1992 | Ricci |
| 5,172,686 | A | 12/1992 | Anthony |
| 5,209,267 | A | 5/1993 | Morin |
| 5,223,996 | A | 6/1993 | Read et al. |
| 5,230,119 | A | 7/1993 | Woods et al. |
| 5,233,996 | A | 8/1993 | Coleman et al. |
| 5,246,254 | A | 9/1993 | LoJacono, Jr. et al. |
| 5,273,032 | A | 12/1993 | Borody |
| 5,284,160 | A | 2/1994 | Dryden |
| 5,307,639 | A | 5/1994 | Boissin |
| 5,308,337 | A | 5/1994 | Bingisser |

(56) References Cited

U.S. PATENT DOCUMENTS

| | | | |
|---|---|---|---|
| 5,335,656 A | 8/1994 | Bowe et al. | |
| 5,341,206 A | 8/1994 | Pittaro et al. | |
| 5,357,948 A | 10/1994 | Ellentropp | |
| 5,365,938 A | 11/1994 | Eskela | |
| 5,367,604 A | 11/1994 | Murray | |
| 5,377,670 A | 1/1995 | Smith | |
| 5,392,770 A | 2/1995 | Clawson et al. | |
| 5,411,474 A | 5/1995 | Ott et al. | |
| 5,427,291 A | 6/1995 | Smith | |
| 5,438,978 A | 8/1995 | Hardester, III | |
| 5,445,874 A | 8/1995 | Shehata | |
| 5,445,875 A | 8/1995 | Persson | |
| 5,454,061 A | 9/1995 | Carlson | |
| 5,461,122 A | 10/1995 | Yilgor et al. | |
| 5,462,048 A | 10/1995 | Lambert et al. | |
| 5,501,212 A | 3/1996 | Psaros | |
| 5,513,634 A | 5/1996 | Jackson | |
| 5,526,849 A | 6/1996 | Gray | |
| 5,532,053 A | 7/1996 | Mueller | |
| 5,537,996 A * | 7/1996 | McPhee | F16L 53/38 392/401 |
| 5,558,087 A | 9/1996 | Psaros et al. | |
| 5,586,551 A | 12/1996 | Hillard | |
| 5,595,174 A | 1/1997 | Gwaltney | |
| 5,599,610 A | 2/1997 | Levy | |
| 5,603,991 A | 2/1997 | Kupiecki et al. | |
| 5,611,332 A | 3/1997 | Bono | |
| 5,614,588 A | 3/1997 | Steenblock et al. | |
| 5,620,500 A | 4/1997 | Fukui et al. | |
| 5,623,922 A | 4/1997 | Smith | |
| 5,630,409 A | 5/1997 | Bono et al. | |
| 5,637,168 A | 6/1997 | Carlson | |
| 5,640,951 A | 6/1997 | Huddart et al. | |
| 5,645,054 A | 7/1997 | Cotner et al. | |
| 5,653,228 A | 8/1997 | Bryd | |
| 5,701,887 A | 12/1997 | Rustad | |
| 5,704,344 A | 1/1998 | Cole | |
| 5,709,762 A | 1/1998 | Rowan | |
| 5,715,647 A | 2/1998 | Keim et al. | |
| 5,722,391 A | 3/1998 | Rosenkoetter et al. | |
| 5,735,266 A | 4/1998 | Smith | |
| 5,738,808 A | 4/1998 | Iwamoto | |
| 5,769,071 A | 6/1998 | Turnbull | |
| 5,794,619 A | 8/1998 | Edelman et al. | |
| 5,794,986 A | 8/1998 | Gansel et al. | |
| 5,798,013 A | 8/1998 | Brandenburger | |
| 5,803,128 A | 9/1998 | Reed | |
| 5,823,184 A | 10/1998 | Gross | |
| 5,848,223 A | 12/1998 | Carlson | |
| 5,850,833 A | 12/1998 | Kotliar | |
| 5,862,651 A | 1/1999 | Stewart et al. | |
| 5,862,652 A | 1/1999 | Schoeler | |
| 5,894,836 A | 4/1999 | Wu | |
| 5,894,839 A | 4/1999 | Rosenkoetter et al. | |
| 5,964,219 A | 10/1999 | Pekka | |
| 5,969,618 A | 10/1999 | Redmond | |
| 5,975,144 A | 11/1999 | Akedo et al. | |
| 5,983,895 A | 11/1999 | Turner | |
| 5,983,896 A | 11/1999 | Fukunaga et al. | |
| 5,992,413 A | 11/1999 | Martin, Jr. et al. | |
| 6,010,118 A | 1/2000 | Milewicz | |
| 6,024,131 A | 2/2000 | Lester et al. | |
| 6,029,660 A | 2/2000 | Calluaud et al. | |
| 6,033,368 A | 3/2000 | Gaston, IV et al. | |
| 6,039,696 A | 3/2000 | Bell | |
| 6,050,260 A | 4/2000 | Daniell et al. | |
| 6,078,730 A | 6/2000 | Huddart et al. | |
| 6,098,615 A | 8/2000 | Lloyd et al. | |
| 6,105,576 A | 8/2000 | Clawson et al. | |
| 6,105,620 A | 8/2000 | Haberi | |
| 6,116,235 A | 9/2000 | Walters et al. | |
| 6,119,694 A | 9/2000 | Correa | |
| 6,148,818 A | 11/2000 | Pagan | |
| 6,167,883 B1 * | 1/2001 | Beran | H05B 3/00 128/203.17 |
| 6,190,480 B1 | 2/2001 | Carlson | |
| 6,192,886 B1 | 2/2001 | Rudolph | |
| 6,192,941 B1 | 2/2001 | Mallen-Herrero et al. | |
| 6,201,223 B1 | 3/2001 | Nitta | |
| 6,237,642 B1 | 5/2001 | Lepoutre | |
| 6,272,933 B1 | 8/2001 | Gradon et al. | |
| 6,302,152 B1 | 10/2001 | Mulligan | |
| 6,349,722 B1 | 2/2002 | Gradon et al. | |
| 6,363,930 B1 | 3/2002 | Clawson et al. | |
| 6,367,472 B1 | 4/2002 | Koch | |
| 6,367,510 B1 | 4/2002 | Carlson | |
| 6,378,520 B1 | 4/2002 | Davenport | |
| 6,394,145 B1 | 5/2002 | Bailly | |
| 6,411,474 B1 | 6/2002 | Anderson | |
| 6,412,481 B1 | 7/2002 | Bienvenu et al. | |
| 6,431,172 B1 | 8/2002 | Bordewick | |
| 6,432,169 B1 | 8/2002 | Kluwe et al. | |
| 6,474,335 B1 | 11/2002 | Lammers | |
| 6,516,798 B1 | 2/2003 | Davies | |
| 6,523,538 B1 * | 2/2003 | Wikefeldt | A61M 16/1075 128/205.12 |
| 6,536,428 B1 | 3/2003 | Smith et al. | |
| 6,536,436 B1 | 3/2003 | McGlothen | |
| 6,539,937 B1 | 4/2003 | Havari | |
| 6,561,219 B1 | 5/2003 | Apostolides | |
| 6,584,972 B2 | 7/2003 | McPhee | |
| 6,595,215 B2 | 7/2003 | Wood | |
| 6,637,434 B2 | 10/2003 | Noble | |
| 6,662,802 B2 | 12/2003 | Smith et al. | |
| 6,667,592 B2 | 12/2003 | Jacobs et al. | |
| 6,684,883 B1 | 2/2004 | Burns | |
| 6,718,973 B2 | 4/2004 | Koch | |
| 6,742,399 B2 | 6/2004 | Kunz et al. | |
| 6,769,431 B2 | 8/2004 | Smith et al. | |
| 6,769,432 B1 | 8/2004 | Keifer | |
| 6,779,522 B2 | 8/2004 | Smith et al. | |
| 6,807,967 B2 | 10/2004 | Wood | |
| 6,973,929 B2 | 12/2005 | Gunaratnam | |
| 6,986,353 B2 | 1/2006 | Wright | |
| 7,086,422 B2 | 8/2006 | Huber et al. | |
| 7,140,366 B2 | 11/2006 | Smith et al. | |
| 7,291,240 B2 | 1/2007 | Smith et al. | |
| 7,468,116 B2 | 12/2008 | Smith et al. | |
| 7,469,719 B2 | 12/2008 | Gray | |
| 7,493,902 B2 | 2/2009 | White et al. | |
| RE40,806 E | 6/2009 | Gradon et al. | |
| 7,559,324 B2 | 7/2009 | Smith | |
| 7,566,486 B2 | 7/2009 | Bourgois et al. | |
| 7,849,885 B2 | 12/2010 | Olsen et al. | |
| 7,900,628 B2 | 3/2011 | Matula et al. | |
| 7,905,232 B2 | 3/2011 | Olsen et al. | |
| 7,958,891 B2 | 6/2011 | Smith et al. | |
| 8,037,882 B2 * | 10/2011 | Smith | A61M 16/0833 128/205.12 |
| 8,220,463 B2 | 7/2012 | White et al. | |
| 8,267,092 B2 | 9/2012 | White et al. | |
| 8,336,570 B2 | 12/2012 | Cardona | |
| 8,851,076 B2 | 10/2014 | White et al. | |
| 8,905,082 B2 | 12/2014 | Gray | |
| 8,980,036 B2 | 3/2015 | Smith et al. | |
| 9,067,035 B2 | 6/2015 | Ophir et al. | |
| 9,533,117 B2 | 1/2017 | Gray | |
| 9,717,874 B2 | 8/2017 | Smith et al. | |
| 9,802,020 B2 | 10/2017 | Smith et al. | |
| 9,827,393 B2 * | 11/2017 | Smith | A61M 16/0875 |
| 9,849,262 B2 | 12/2017 | White et al. | |
| 9,878,120 B2 | 1/2018 | White et al. | |
| 10,159,814 B2 | 12/2018 | Smith et al. | |
| 10,220,175 B2 | 3/2019 | White et al. | |
| 10,228,082 B2 | 3/2019 | De Nora | |
| 10,252,017 B2 | 4/2019 | Smith et al. | |
| 10,286,174 B2 | 5/2019 | Smith et al. | |
| 10,350,376 B2 | 7/2019 | White et al. | |
| 10,478,583 B2 | 11/2019 | Gray | |
| 10,953,184 B2 * | 3/2021 | Smith | A61M 16/142 |
| 11,219,733 B2 | 1/2022 | Gray | |
| 2001/0054422 A1 | 12/2001 | Smith et al. | |
| 2002/0002976 A1 | 1/2002 | Smith et al. | |
| 2002/0017330 A1 | 2/2002 | Armenia et al. | |

(56) References Cited

U.S. PATENT DOCUMENTS

| | | |
|---|---|---|
| 2002/0046755 A1 | 4/2002 | De Voss |
| 2002/0055685 A1 | 5/2002 | Levitsky et al. |
| 2002/0059935 A1 | 5/2002 | Wood |
| 2002/0170940 A1 | 11/2002 | Kazama et al. |
| 2002/0195104 A1 | 12/2002 | Fini et al. |
| 2003/0028139 A1 | 2/2003 | Inoue |
| 2003/0047185 A1 | 3/2003 | Olsen et al. |
| 2003/0051795 A1 | 3/2003 | Burgess |
| 2003/0062048 A1 | 4/2003 | Gradon et al. |
| 2003/0070680 A1 | 4/2003 | Smith et al. |
| 2003/0094178 A1 | 5/2003 | McAuley et al. |
| 2003/0213490 A1 | 11/2003 | Righetti |
| 2004/0045549 A1 | 3/2004 | Smith et al. |
| 2004/0065335 A1 | 4/2004 | Huber et al. |
| 2004/0079371 A1 | 4/2004 | Gray |
| 2004/0081784 A1 | 4/2004 | Smith et al. |
| 2004/0099268 A1 | 5/2004 | Smith et al. |
| 2004/0118401 A1 | 6/2004 | Smith et al. |
| 2004/0250815 A1 | 12/2004 | Scott et al. |
| 2005/0115622 A1 | 6/2005 | Bennett et al. |
| 2005/0176331 A1 | 8/2005 | Martin |
| 2005/0247362 A1 | 11/2005 | Harcourt |
| 2006/0081303 A1 | 4/2006 | Coleman |
| 2006/0162726 A1 | 7/2006 | Smith et al. |
| 2007/0235100 A1 | 10/2007 | Tomerlin et al. |
| 2008/0072986 A1 | 3/2008 | Burrowes et al. |
| 2009/0025724 A1 | 1/2009 | Herron, Jr. |
| 2009/0078260 A1 | 3/2009 | Smith et al. |
| 2009/0088656 A1 | 4/2009 | Levitsky et al. |
| 2009/0126817 A1 | 5/2009 | Gray |
| 2011/0054422 A1 | 3/2011 | Locke et al. |
| 2012/0090622 A1 | 4/2012 | Chang |
| 2013/0098360 A1 | 4/2013 | Hurmez et al. |
| 2014/0180157 A1 | 6/2014 | Levitsky et al. |
| 2014/0373843 A1 | 12/2014 | Gray |
| 2015/0083125 A1 | 3/2015 | White et al. |
| 2015/0165155 A1 | 6/2015 | Smith et al. |
| 2015/0208953 A1 | 7/2015 | Levitsky et al. |
| 2015/0306333 A1 | 10/2015 | Armadio et al. |
| 2016/0045702 A1 | 2/2016 | Milne et al. |
| 2017/0080175 A1 | 3/2017 | Gray |
| 2017/0087235 A1 | 3/2017 | Wright |
| 2017/0087323 A1 | 3/2017 | White et al. |
| 2017/0087325 A1 | 3/2017 | White et al. |
| 2017/0119989 A1 | 3/2017 | White et al. |
| 2017/0296769 A1 | 10/2017 | Smith et al. |
| 2018/0071477 A1 | 3/2018 | Smith et al. |
| 2018/0071478 A1 | 3/2018 | Smith et al. |
| 2018/0133428 A1 | 5/2018 | Smith et al. |
| 2019/0111228 A1 | 4/2019 | Smith et al. |
| 2019/0201649 A1 | 7/2019 | Smith et al. |
| 2019/0224439 A1 | 7/2019 | Lopez et al. |
| 2019/0366028 A1 | 12/2019 | White et al. |
| 2020/0147334 A1 | 5/2020 | Gray |
| 2021/0016043 A1 | 1/2021 | Smith et al. |

FOREIGN PATENT DOCUMENTS

| | | | |
|---|---|---|---|
| AU | 200013529 | | 6/2000 |
| AU | 200143823 A1 | | 11/2001 |
| CA | 2833707 | | 11/2001 |
| CA | 2346628 | | 7/2010 |
| CA | 2697142 | | 2/2014 |
| DE | 28036 | | 2/1984 |
| DE | 19647548 A1 | | 5/1998 |
| DE | 19716977 | | 11/1998 |
| DE | 19949283 A1 | | 4/2001 |
| DE | 19958296 C1 | | 9/2001 |
| DE | 19848172 | | 11/2002 |
| EP | 0535379 | | 4/1993 |
| EP | 0557040 | | 8/1993 |
| EP | 0567158 | | 10/1993 |
| EP | 0621050 | | 10/1994 |
| EP | 0747078 | | 11/1996 |
| EP | 0806217 A2 | | 11/1997 |
| EP | 0815792 | | 1/1998 |
| EP | 0935971 | | 8/1999 |
| EP | 0936389 | | 8/1999 |
| EP | 1014527 | | 6/2000 |
| EP | 1166814 | | 1/2002 |
| EP | 1396276 | | 3/2004 |
| EP | 0885623 | | 11/2004 |
| EP | 1524937 | | 4/2005 |
| EP | 1557257 | | 7/2005 |
| EP | 1477200 | | 10/2006 |
| EP | 1153627 | | 11/2007 |
| EP | 1885460 | | 2/2008 |
| EP | 1681071 | | 2/2009 |
| EP | 2226341 | | 9/2010 |
| EP | 2305336 | | 4/2011 |
| EP | 2025359 | | 9/2013 |
| EP | 2666795 | | 11/2013 |
| FR | 2287637 | | 5/1976 |
| FR | 2638361 | | 5/1990 |
| FR | 2762309 | | 10/1998 |
| GB | 9683 | | 4/1909 |
| GB | 587163 | | 4/1947 |
| GB | 859613 | | 1/1961 |
| GB | 863105 | | 3/1961 |
| GB | 863106 | | 3/1961 |
| GB | 1463083 | | 2/1977 |
| GB | 1492459 | | 11/1977 |
| GB | 2024100 | | 1/1980 |
| GB | 2284356 | | 6/1985 |
| GB | 2252515 | | 8/1992 |
| GB | 2139110 | | 11/1994 |
| JP | S62-236724 | | 10/1987 |
| JP | 63-272530 | | 11/1988 |
| JP | H02118555 | | 9/1990 |
| JP | H0353254 | | 5/1991 |
| JP | H03-168155 | | 7/1991 |
| JP | H05-052378 | | 3/1993 |
| JP | H05317428 | | 12/1993 |
| JP | H06-023051 | | 2/1994 |
| JP | H0623051 | | 2/1994 |
| JP | H076909 | | 2/1995 |
| JP | H09-234247 | | 9/1997 |
| JP | 10-248935 | | 9/1998 |
| JP | 11-323899 A | | 11/1999 |
| JP | 2000-24111 | | 1/2000 |
| JP | 2000-24113 | | 1/2000 |
| JP | 2001-179822 | | 7/2001 |
| WO | WO 88/01903 | | 3/1988 |
| WO | WO 95/16746 | | 6/1995 |
| WO | WO 95/33163 | | 12/1995 |
| WO | WO 97/18001 | | 5/1997 |
| WO | WO-9718001 A1 * | 5/1997 | ............ A61M 16/08 |
| WO | WO 1997/23543 | | 7/1997 |
| WO | WO 98/02199 | | 1/1998 |
| WO | WO 98/24500 | | 6/1998 |
| WO | WO 98/41148 | | 9/1998 |
| WO | WO 99/64077 | | 12/1999 |
| WO | WO 00/48682 | | 8/2000 |
| WO | WO 01/41854 | | 6/2001 |
| WO | WO 01/49351 | | 7/2001 |
| WO | WO 2006/120683 | | 11/2006 |
| WO | WO 2012/077052 | | 6/2012 |

OTHER PUBLICATIONS

U.S. Appl. No. 10/622,755, filed Jul. 18, 2003, Smith et al.
U.S. Appl. No. 10/653,821, filed Sep. 3, 2003, Gray.
U.S. Appl. No. 10/656,574, filed Sep. 5, 2003, Smith et al.
U.S. Appl. No. 11/862,875, filed Sep. 27, 2007, Smith et al.
U.S. Appl. No. 12/275,710, filed Nov. 21, 2008, Gray.
Adams et al., "Thermoplastic Polyether Ester Elastomers"; Supplied by British Library; unknown date.
Australian Patent Application No. 200143823 Published on Nov. 15, 2001 entitled Components for Breathing Circuits; Inventors Smith, Baldwin, Powell and Millar.
BS 6151:1992 (ISO 5367:1991), British Standard, Specification for Breathing tubes for use with anaesthetic apparatus and ventilators, in 12 pages.

(56) References Cited

OTHER PUBLICATIONS

Dryers, Sampling Systems, dated Jan. 27, 1999, Perma Pure, www.permapure.com capture from archive.org.
Etnier, Shelley A., Flexural and Torsional Stiffness in Multi-Jointed Biological Beams; Published in Biological Bulletin; Copyright 2001; Eight pages.
Farley, R.D. and Franklin, D.H., "Development of a humidifier for patient ventilation using a semi-permeable tube to minimize system condensate," J. Biomed. Eng., vol. 14, Sep. 1992.
Flow of Fluids through Valves, Fittings, and Pipe; Crano Co., 1999.
Gibson; Effect of Temperature on Water Vapor Transport Through Polymer Membrane Laminates; U.S. Army; Feb. 1999.
Gibson; Measurement of water vapor diffusion through laminated fabrics and membranes using a diode laser spectroscope; US Army; Jan. 1998.
Gibson; On the Flow of Water through Pipes and Passages having converging or Diverging Boundaries; Univ. College, Dundee; Oct. 10, 1909.
Gravenstein; Gas Monitoring in Clinical Practice; Butterworth-Heinemann; 1995.
Hytrel thermoplastic polyester elastomer from E.I. du Pont de Nemours and Company, 63 pages, Copyright 2000.
Information Disclosure Statement Transmittal Letter submitted in U.S. Appl. No. 10/653,821, dated Dec. 10, 2003.
Information Disclosure Statement Transmittal Letter submitted in U.S. Appl. No. 10/653,821, dated Dec. 5, 2003.
Johnson-Schultze; Breathable TPE Films for Medical Applications; Medical Device & Diagnostic Industry Magazine; Jul. 1, 2000.
Machine translation of German Patent 19848172, date unknown.
MBM-200 Deltatrac II Service Manual; Datex/Division of Instrumentarium Corp; Mar. 1, 1993.
Medical Gas Dryers, dated Oct. 17, 2000, Perma Pure, www.permapure.com capture from archive.org.
ME-Series Moisture Exchangers, Mar. 3, 2001, Perma Pure, www.permapure.com capture from archive.org.
MR700/MR720/MR730 Respiratory Humidifiers Operator's Manual, Printed Mar. 1998, Fisher & Paykel Healthcare.
One page off the Perma Pure Inc. website of the product brochure #104 of the New PD TM—Series Gas Dryers.
Painter, Chris J., "Waterproof, Breathable Fabric Laminates: A Perspective from Film to Market Place", Journal of Coated Fabrics, vol. 26, Oct. 1996, pp. 107-130.
Perma Pure Dryers Bulletin 104, No date, at least as early as Dec. 14, 1992.
Smart Anesthesal Multi-Gas SAM/SAM-80 Module Field Service Manual; Marquette Medical Systems; Mar. 27, 1998.
Sparrow, E.M. et al., Flow Serparation in a Diversging conical duct: Effect of Reynolds number and divergence angle; International Journal of Heat and Mass Transfer; Jun. 2009.
Stroeks et al., "Modeling the moisture vapour transmission rate through segmented block co-poly(ether-ester) based breathable films," Polymer, vol. 42, Issue 1, Jan. 2001, pp. 117-127.
Three pages off the SympaTex website of some of the most common questions that are asked and some technical data on the SympaTex membrane.
May 3, 2019 Complaint for Patent Infringement Demand for Jury Trial, *Fisher & Paykel Healthcare Limited* v. *Flexicare Incorporated*, Case No. 8:19-CV-00835.
Fisher & Paykel Healthcare Limited's Disclosure of Asserted Claims and Infringement Contentions, *Fisher & Paykel Healthcare Limited* v. *Flexicare Incorporated*, Case No. 8:19- CV-00835JVS(DFMx), Aug. 19, 2019, in 17 pages.
Exhibit A, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 34 pages.
Exhibit B, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 16 pages.
Exhibit C, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 31 pages.
Exhibit D, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 15 pages.
Exhibit E, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 16 pages.
Exhibit F, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 34 pages.
Exhibit G, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 24 pages.
Exhibit H, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 27 pages.
Exhibit I, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 34 pages.
Exhibit J, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 29 pages.
Flexicare Incorporated's Patent L.R. 3-3 Invalidity Contentions, *Fisher & Paykel Healthcare Limited* v. *Flexicare Incorporated*, Case No. 8:19-CV-00835JVS(DFMx), Oct. 17, 2019, in 54 pages.
Canadian Examination Report for Application No. CA 2,697,142 dated Jun. 27, 2012; 2 pages.
Canadian Examination Report; dated Apr. 6, 2016 in 3 pages.
Canadian Office Action dated Mar. 11, 2015 for Canadian Application No. 2833707.
European Examination Report for European Patent Application 17202695.7 dated Aug. 19, 2020, 4 pages.
European Examination Report for European Patent Application 17202695.7 dated Oct. 4, 2019.
European Search Report for Application No. 10184899.2 dated Mar. 7, 2011; 3 pages.
European Search Report, Application No. 17202695.7; dated Aug. 3, 2018.
Extended European Search Report for Application No. 10182233.6, dated Oct. 20, 2015.

\* cited by examiner

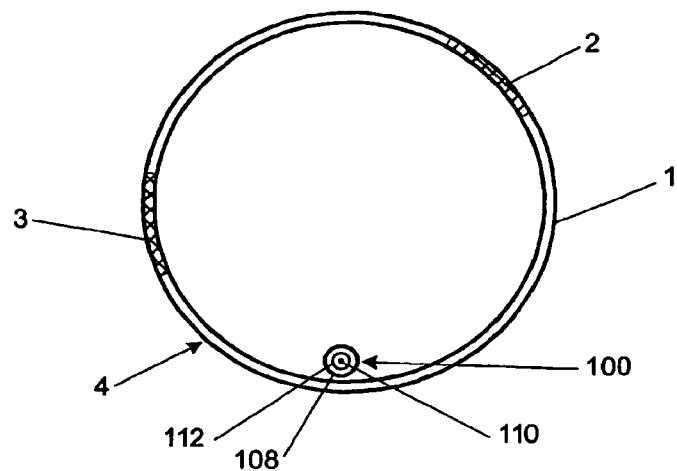
FIG. 1A
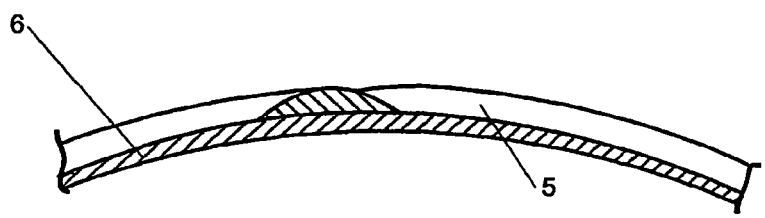
FIG. 2
FIG. 3
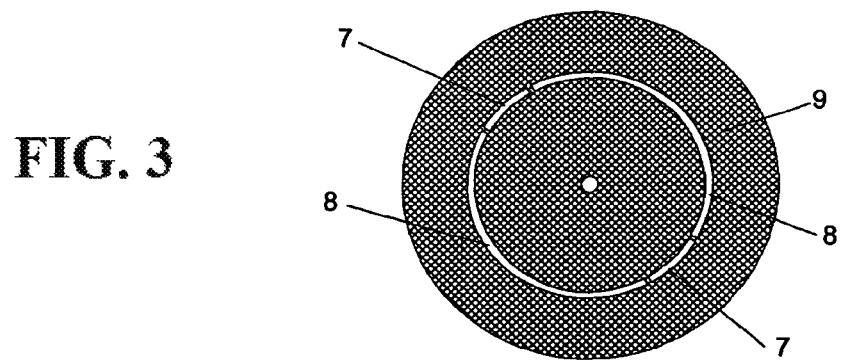

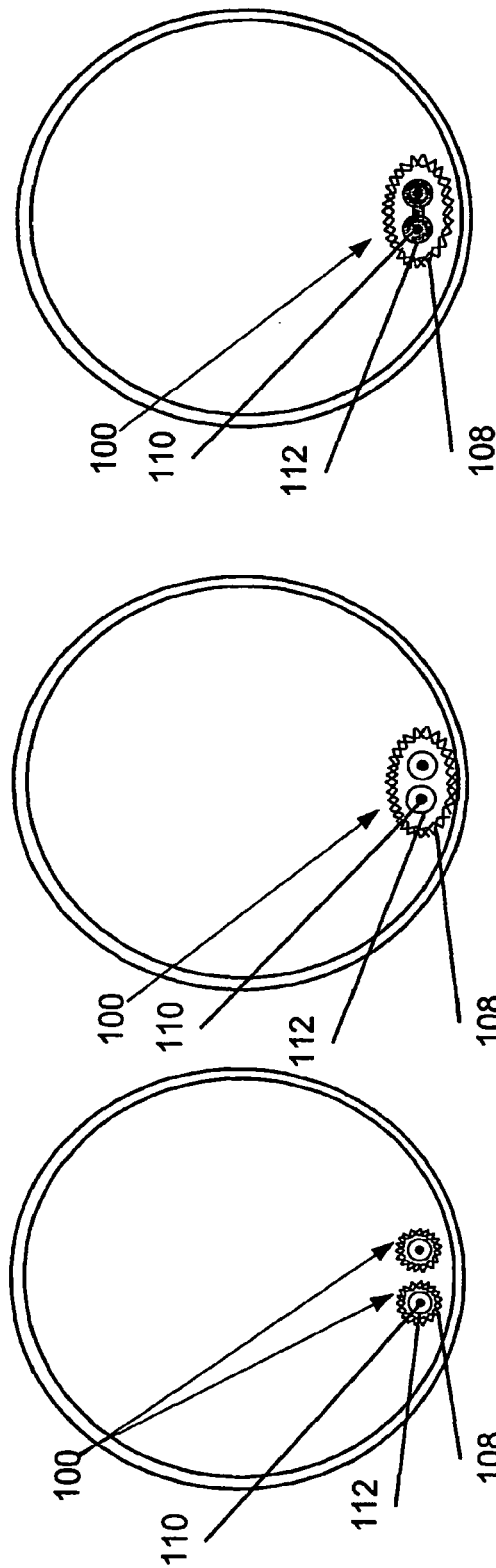
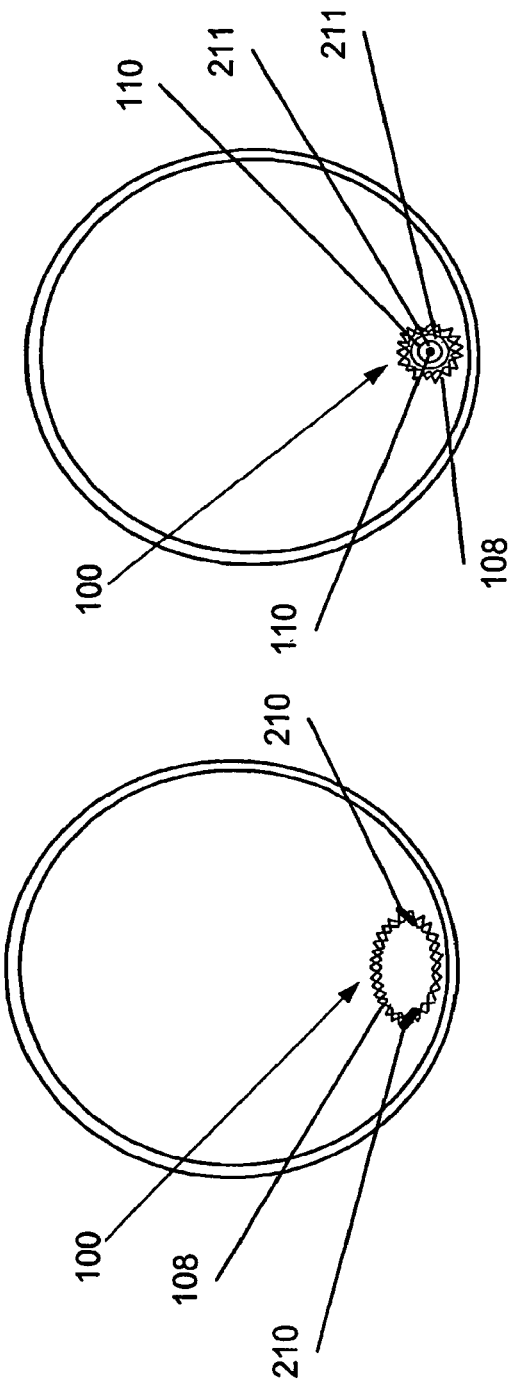
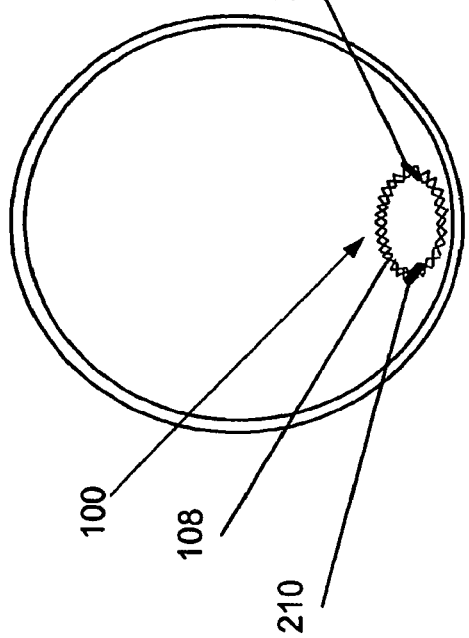

CONDUIT WITH HEATING ELEMENT

CROSS-REFERENCE TO RELATED APPLICATIONS

This application is a continuation of U.S. patent application Ser. No. 15/789,827, filed on Oct. 20, 2017, which is a continuation of Ser. No. 13/272,047, entitled "Conduit With Heated Wick," filed on Oct. 12, 2011 and issued as U.S. Pat. No. 9,827,393 on Nov. 28, 2017, which is a continuation of U.S. patent application Ser. No. 10/684,917, entitled "Conduit With Heated Wick," filed on Oct. 14, 2003 and issued as U.S. Pat. No. 8,037,882 on Oct. 18, 2011, all of which are hereby incorporated by reference in their entirety.

BACKGROUND OF THE INVENTION

Field of the Invention

The present invention relates to conduits and in particular to conduits for use in a breathing circuit.

Description of the Related Art

In assisted breathing, particularly in medical applications, gases having high levels of relative humidity are supplied and returned through conduits of a relatively restricted size. Build up of condensation on the inside wall of the conduit is a frequent result of this high humidity. In the prior art, attempts have been made to reduce the adverse effect of this condensation by either reducing the level of condensation or providing collection points in the conduit for draining condensed liquid from the conduit. Reducing the condensation has generally been by maintaining or elevating the temperature of the gases flow and/or of the conduit wall to reduce the formation of condensation.

SUMMARY OF THE INVENTION

It is an object of the present invention to provide a conduit, which will at least go some way towards improving on the above or which will at least provide the public and the medical profession with a useful choice.

In a first aspect the invention consists in a conduit for a breathing circuit including heating means located within said conduit, said heating means comprising an elongate heating element covered with an inner electrical insulating layer and at least partially covered with an outer hydrophilic layer, there being no means for direct supply of water or fluid to said hydrophilic layer from outside said conduit.

In a second aspect the invention consists in a breathing circuit including an expiratory gases flow path and a heating means located within said expiratory gases flow path and associated at least-in part with a portion of hydrophilic material.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

FIGS. 1A-1D are cross sectional elevations of conduits for the expiratory limb of a breathing circuit according to the present invention.

FIG. 2 is a cross sectional view of a section of conduit wall according to one possible construction.

FIG. 3 is a cross sectional view of a co extrusion die head for extruding a conduit including two longitudinal strips of permeable material, similar to the conduits of FIGS. 1A-1D.

FIG. 9A-9E are cross sectional views of conduits including a heated wick according to further embodiments of the present invention.

DETAILED DESCRIPTION OF THE PREFERRED EMBODIMENT

The present invention involves the provision of a heated wick within one of the lengths of conduit making up a breathing circuit. By heated wick we refer to a heater associated with a hydrophilic layer. The heated wick is disposed freely within the conduit so that at least part of it lays in low points of the conduit at which condensation accumulates. Accumulated condensation is absorbed by the hydrophilic layer and re-evaporated by heat from the heater.

Figure 7:
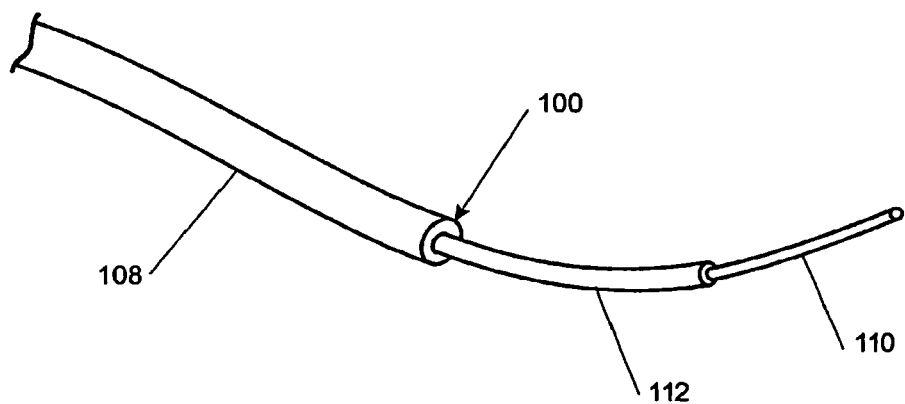
FIG. 7 is a cut-away perspective view of a heated wick according to a further aspect of the present invention.

As seen in FIGS. 1A and 7 the heated wick 100 is comprised of an outer hydrophilic layer 108, covering an inner insulating hydrophobic layer 112, which in turn covers a heater element 110. Any water that collects in the conduit 102 is attracted to and drawn into the hydrophilic layer 108, and is then re-vaporised as it is heated by the heater element 110. The intermediate hydrophobic insulating layer 112 is provided to electrically insulate the inner heater element 110 from the rest of the system.

Such a heated wick 100 as shown in FIG. 7 may be constructed by coextruding the hydrophobic insulating layer 112 and hydrophilic layer 108 onto the heater wire 110. Suitable materials for the hydrophilic layer include polyester or polyurethane foam, or a braid of hydrophilic material e.g. cotton. Suitable materials for the hydrophobic insulating layer include polypropylene or silicone coatings.

Figure 1D:
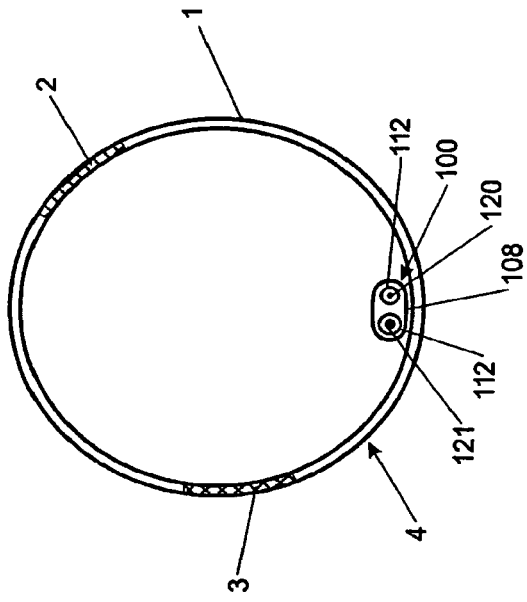
Figure 1B:
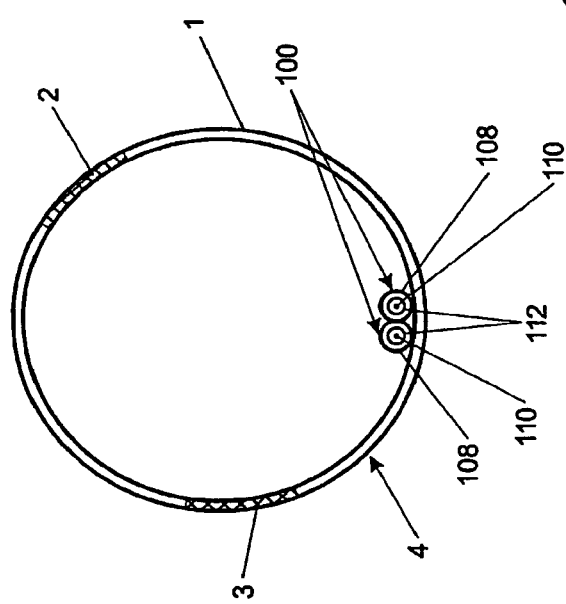
Figure 1C:
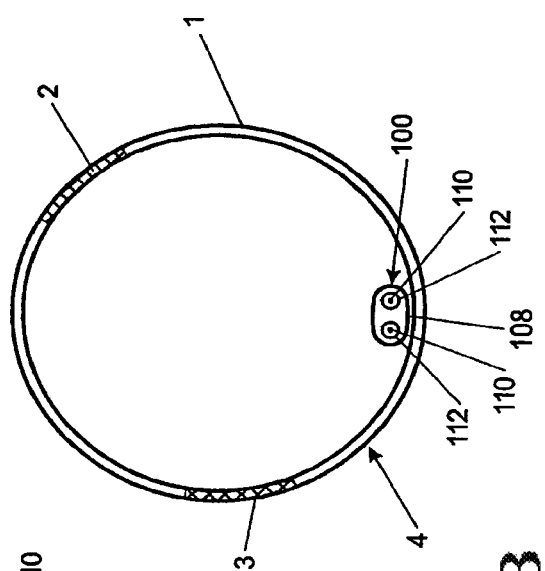

An alternate form for the heated wick is shown in each of FIGS. 1B, 1C and 1D. In FIG. 1B the heated wick includes a looped back heater element 110, coated in a hydrophobic insulating layer 112, and the whole encased within a hydrophilic surrounding layer 108. In a further variation depicted in FIG. 1C the heater element is an electrical resistance heater and includes a length 120 of higher resistance and a length 121 of lower resistance, insulated from one another and joined at their remote ends. In a still further variation depicted in FIG. 1D the heated wick 100 is disposed in the conduit as a simple loop. Each of these variations provide both ends of the heated wick at the same end of the conduit, allowing a single connection of the heater element to an energising source. The embodiment of FIG. 1C has the additional advantage that the heater element voltage at the remote end will be lower than half the supply voltage, and with appropriate selection can be very close to zero.

Alternatively the hydrophilic layer 108 may achieve its hydrophilic (water attracting effect), through its physical structure and capillary action rather than an inherent property of the material composition. It is to be understood that references to the outer hydrophilic layer 108 throughout the specification may refer to the overall hydrophilic nature of the layer 108. The hydrophilic layer 108 may be constructed from a hydrophilic material composition or alternatively may be constructed from water resistant materials but have a physical structure configured so water "soaks" into or is attracted to the layer 108 through capillary action. Alternative constructions of the surrounding hydrophilic layer 108 are shown in FIGS. 9A to 9D and FIGS. 10 and 11.

For example, as seen in FIG. 9A the heated wick 100 is comprised of an inner insulating layer 112 which covers a heater element 110. The heater element 110 and the insulating layer 112 are encased in an outer hydrophilic layer 108, which is comprised of a braided sheath. The braided filaments may be of a water resistant material such as polyethylene terepythalate (PET), polyethylene or polypropylene. In use, liquid water or condensate is drawn into the spaces between the filaments of the braided sheath by capillary action thus giving layer 108 a water attracting or hydrophilic effect.

An alternative form of the heated wick is shown in each of FIGS. 9B, 9C and 9D. The construction shown in FIG. 9B is analogous to that described previously and shown in FIG. 1B, except that the hydrophilic surrounding layer 108 is a braided sheath similar to that shown in FIG. 9A. A variation of the structure shown in FIG. 9B is shown in FIG. 9C. In this embodiment the hydrophobic insulating layer 112 encapsulates both the positive and negative heater wire strands together.

A further alternative form of the heated wick is shown in FIG. 9D. In this embodiment the heater wire(s) are provided by conductive strands 210 which are braided into the braided mesh. In this embodiment a pair of conductive heater wire strands 210 are coated in an electrical insulating material and braided into a mesh tube in order that the heated wick can attract water to itself through capillary action. It will be appreciated that a single heater wire or multiple wires may be advantageous.

FIG. 9E show a heated wick embodiment where the positive and negative heater wires are arranged co-axially. In this embodiment a pair of heater wires 110, are shown. Each heater wire is surrounded by an electrical insulating layer 211, and each is arranged co-axially. An outer water attracting braided sheath 108 surrounds the heater wires to give the construction a wicking effect due to capillary action.

Figures 10, 11:
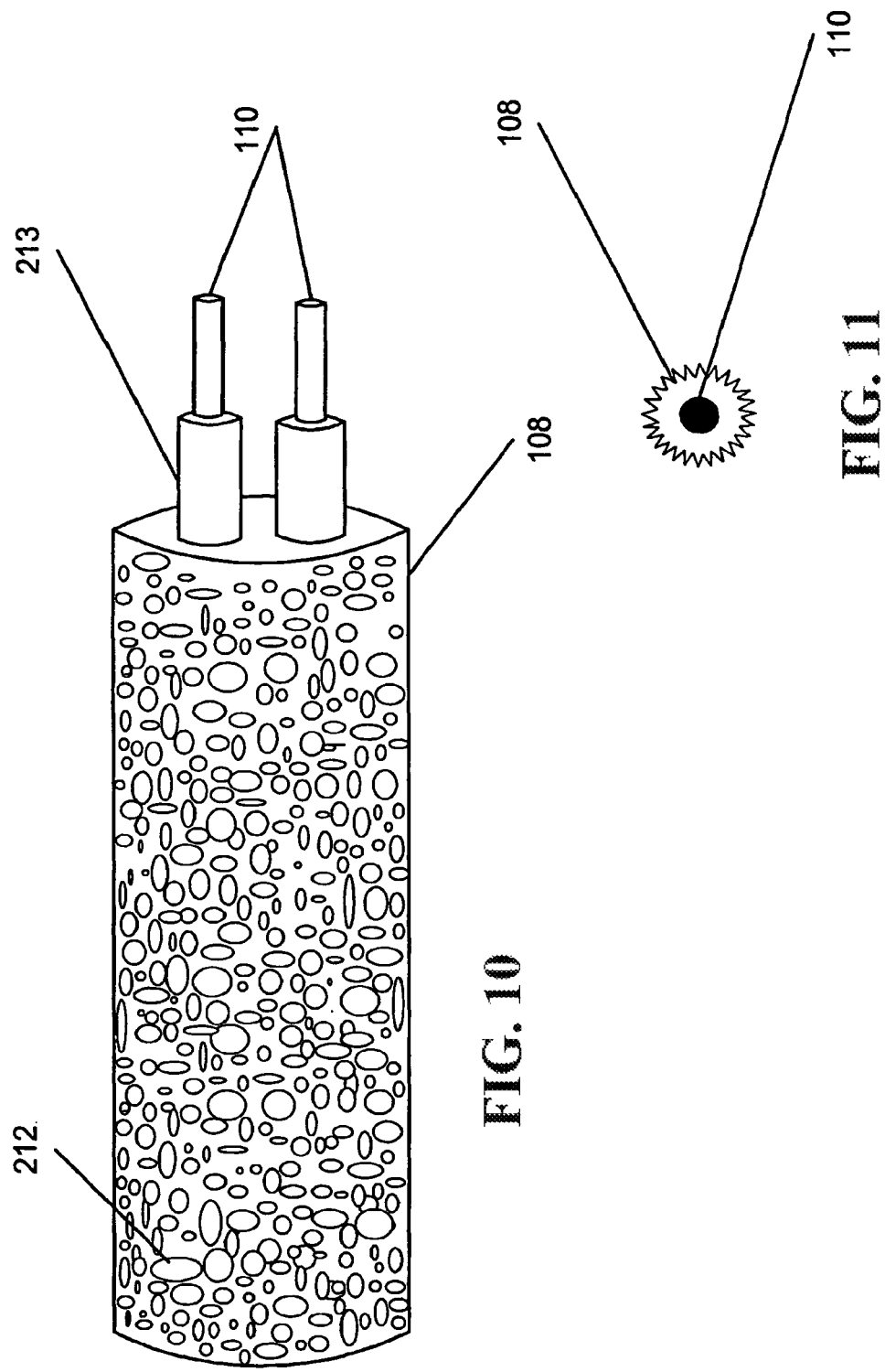
FIG. 10 is a cross sectional view of a conduit including a heated wick according to a still further embodiment of the present invention.
FIG. 11 is a cross sectional view of a conduit including a heated wick according to a still further embodiment of the present invention.

Alternatives to the braided mesh embodiment are shown in FIGS. 10 and 11. In these embodiments the outer hydrophilic layer 108 is constructed from a water resistant material (for example PET) and attracts water into spaces and voids 212 on the outer surface of the layer 108 through capillary action. The hydrophilic layer 108, shown in FIG. 10 is formed from a partially foamed plastic layer which encases the insulated conductive wire(s). The outer layer is covered in voids or pores 212, in order that the heated wick can attract water to itself through capillary action. Alternatively, the outer layer may be formed by sintering. Heater element(s) 110 are imbedded in layer 108, and may also include an electrical insulating layer 213.

An alternative structure of a non-braided layer 108 constructed from a water resistant material is shown in FIG. 11. In this embodiment the outer layer 108 includes a number of grooves and/or fins in order to allow the wick to attract water though capillary action. The grooves may be substantially axial, annular, helical or knurled in a criss-cross fashion.

The heated wick may also be provided in both the inspiratory and expiratory conduits. In this case a single length of heated wick may run down the inspiratory conduit and back up the expiratory conduit, with the ends of the conduits being insufficiently close proximity to enable easy electrical connection to both ends.

The heated wick is provided with connections at its ends for connecting to an energising source. The ends of the wick may be directly electrically connected to electrical connectors in the connector of the tube or conduit. These connectors may for example be a socket for receiving a plug from a voltage source. Alternatively the heated wick may be a fixture of an assisted breathing device, such as a ventilator or humidifier, and may extend from within the breathing conduit connection port of the device, or be plugged into a socket within such port. Many other configurations for supplying power to the heated wick will also suggest themselves.

Figure 6:
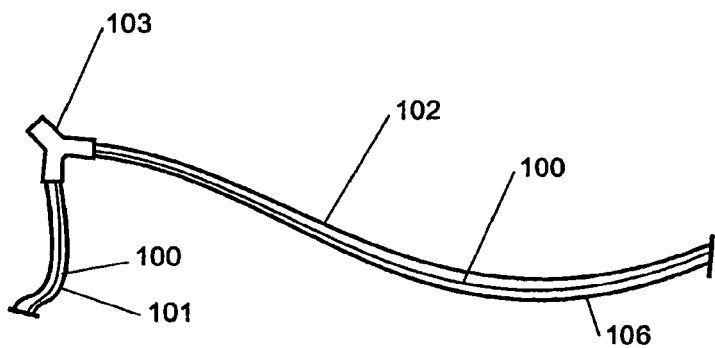
FIG. 6 is a representation of a breathing circuit with an expiratory limb fashioned according to the present invention and including a heated wick according to a further aspect of the present invention.

The heater element 110 is also effective to supply heat to the gases stream to reduce the overall level of condensation occurring within the conduit. At the same time any condensation that does occur is sucked up by the wick and re-evaporated by heat from the heater element 110. Accordingly where a heated wick is provided in the inspiratory arm of the breathing circuit humidity supplied to the gases stream prior to entry into the breathing circuit is not lost through condensation, instead being re-evaporated by the heated wick. This reduces the total humidification load of the breathing circuit as well as eliminating the requirement for conduit drainage ports.

Where the heated wick is provided in the expiratory conduit it eliminates the need for conduit drainage ports. Furthermore it provides additional advantages when used in conjunction with an expiratory conduit in which at least a part of the conduit wall is formed from a breathable material. Such an arrangement is shown in FIG. 6.

A breathable material, as used herein, is a material that allows the passage of water vapour without allowing the passage of liquid water or respiratory gases. Materials may be breathable due to their composition, physical structure a combination thereof.

One such breathable material is an activated perfluorinated polymer material having extreme hydrophilic properties. An example of this polymer material is marketed under the trade mark NAFION by DuPont Fluoro products of Fayetteville USA. This material is useful due to its extreme hydrophilic properties and due to its ability to be extruded, particularly to be co-extruded in combination with other plastic materials.

Alternative materials are also envisaged including:
    (a) Hydrophilic thermoplastics,
    (b) woven treated fabric products exhibiting breathable characteristics The preferred material is a hydrophilic polyester block copolymer formed into a homogeneous flat film. An example of such a film is sold under the brand SYMPATEX. This material is particularly suited to thin film productions.

An example of application of the conduit with heated wick is shown in FIG. 6. A heater element 110 coated with a hydrophilic layer, runs the length of the semi-permeable conduit 102 and the inspiratory conduit 101. During operation humidified gases are drawn through inspiratory conduit 101, then flow through the Y connector 103, and are then delivered to the patient (not shown). When the patient expires the gases flow through the Y connector 103, and then flow through the breathable expiratory conduit 102. The expiratory gases will be almost saturated with humidity and as the wall of the breathable expiratory conduit 102 will be relatively cool, some portion of the vapour in the gases will condense and therefore water will collect in the conduit and run towards the lowest point 106. As already mentioned such collection of water is undesirable and therefore the heated wick 100 is provided to revaporise the water that collects. This is particularly important where the breathable material is one, such as SYMPATEX, which transmits water vapour but does not transmit liquid water. While such materials are advantageous for their ability to stop harmful bacteria and viruses this advantage is offset by their inability to transmit liquid water. By re-evaporation of any collected water by the heated wick it can be transmitted through the breathable membrane in its vapour state.

Referring to FIGS. 1A-1D, in one embodiment, the conduit 4 of the expiratory limb of a breathing circuit is formed having one or more longitudinal strips 2, 3 of breathable membrane as part of the wall 1 thereof.

Figure 8:
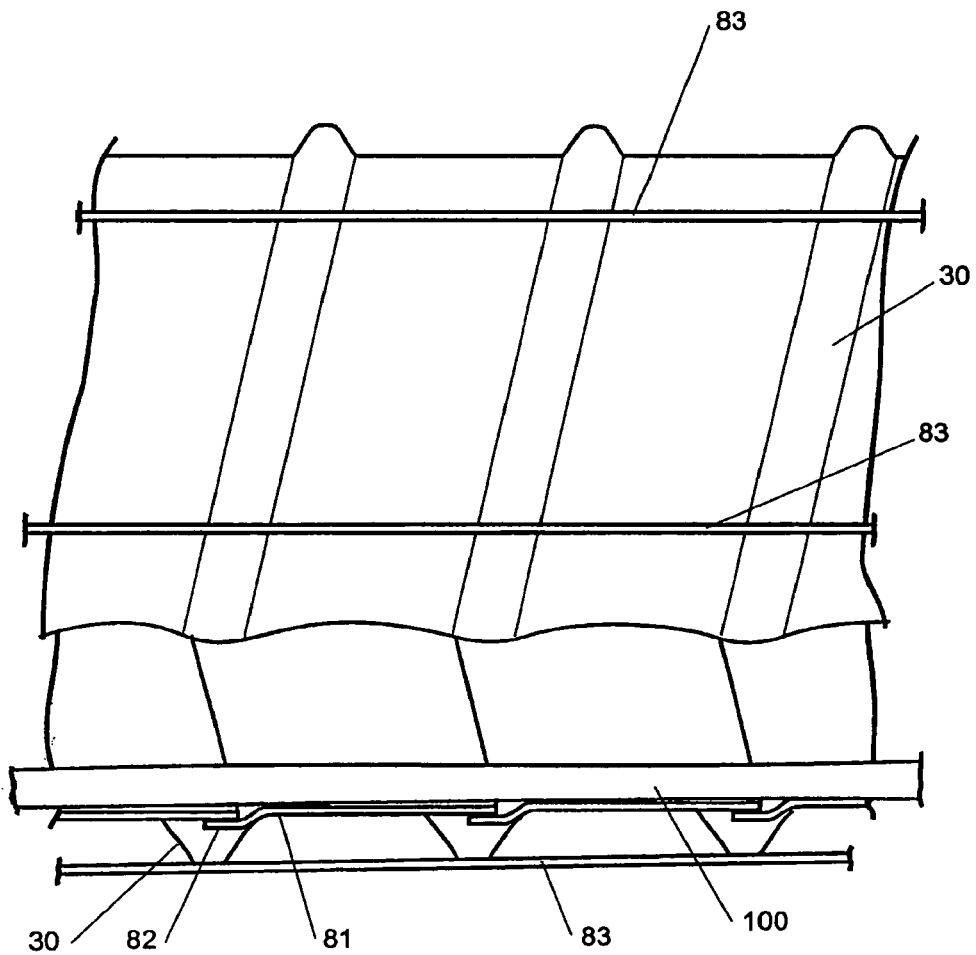
FIG. 8 is a side elevation partially in cross section of an expiratory limb conduit according to a further embodiment of the present invention.

Referring to FIG. 8 an alternative embodiment of the expiratory limb conduit is shown in which the entire flexible wall membrane of the conduit is formed from a breathable plastic membrane, extruded and wound helically with edges of adjacent turns sealed to one another.

Figure 4:
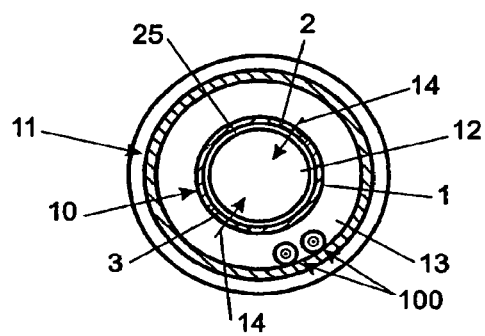
FIG. 4 is a cross sectional elevation of a coaxial breathing circuit according to a further embodiment of the present invention incorporating a heated wick in the expiratory gases flow path.
Figure 5:
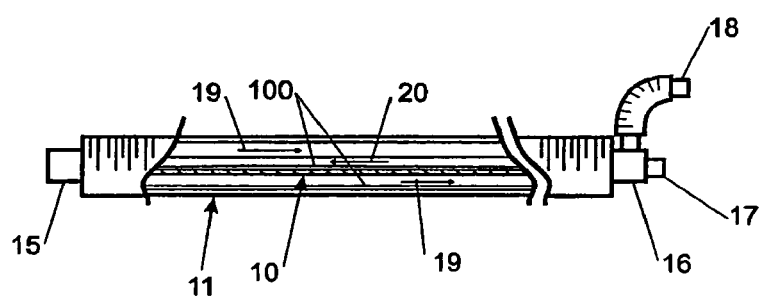
FIG. 5 is a side elevation in partial cross section of a coaxial breathing circuit including a heated wick in both the inspiratory and expiratory gases flow paths.

Referring to FIGS. 4 and 5, further aspects is shown in which an expiratory limb conduit according to the present invention is provided as a gases flow path of a coaxial conduit configuration, such that expiratory gases and inspiratory gases each flow in one of the inner conduit or the space between the inner conduit and the outer conduit and in use water vapour but not liquid water is transmitted from the expiratory gases passageway to the inspiratory gases passageway.

Referring to FIGS. 2 & 8, spiral or helical internal (or external) reinforcing members 30, or a series of annular hoop reinforcing members, may be provided outside (or inside) the tubular membrane 6 to provide support to it. The helical, spiral or hoop supporting members may for example be formed from polymer plastic materials, such as the material used in the wall of the conduit (not being the breathable regions), or alternatively may for example be a metal wire support, such as drawn steel wire.

The conduit shown in FIG. 2 may be formed in any one of a number of methods. For example the tubular membrane 6 may be supplied in a continuous tube. Alternatively it might be supplied in tape form, which may result in the conduit of FIG. 8. Supplied as extruded tape 81, the membrane may be wound helically onto a former. The helical supporting rib 30, provided in a breathable molten state is then laid on the overlap between adjacent turns. The heat from the helical supporting rib 30 bonds the two adjacent strips with itself forming a flexible resilient conduit once cooled.

Referring to FIG. 8 an additional longitudinal reinforcement may be provided to alleviate the shortcomings of some of the breathable materials. This reinforcement may be in the form of a plurality of reinforcing threads 83. The threads 83 run parallel to the length of the conduit and are supported on the helical reinforcing ribs, spanning between them. As many threads may be provided. For example eight threads may be spaced around the circumference of the tube. The reinforcing threads 83 stop accidental stretching of the conduit, and providing they have some stiffness and the rib spacing is not to large, also reduce any longitudinal compression of the conduit under negative relative internal pressures.

Referring to FIG. 3 the conduit, such as that shown in FIGS. 1A-1D, may alternatively be formed by co extrusion of the breathable material (where the material is a suitable extrudable material) with a plastic material forming the remainder of the conduit wall. A suitable co extrusion die 9 is depicted in FIG. 3 in which a pair of circumferential sections 7 of the die opening have the breathable plastic material extruded therethrough, and the remainder sections 8 of the annular extrusion opening have the non permeable plastic wall material extruded therethrough.

The purpose of the breathable region or regions of the conduit wall is to allow diffusion of water vapour (and for some materials liquid water) from the expiratory limb of the breathing circuit along the path thereof independent of specific drain locations. This eliminates the build up of condensation within the expiratory limb by drying the humidified gases during their flow through the expiratory limb. This furthermore reduces the humidity of the gases arriving at ancillary equipment, such as filters, ventilators and the like reducing the risk of condensation accumulation, thereby improving their operation.

In accordance with a further aspect of the invention, and as exemplified in FIGS. 4 and 5 the conduit incorporating one or more longitudinal strips of breathable membrane may further be incorporated in a coaxial breathing circuit as a passive humidification device. In particular referring to the cross section in FIG. 4 the coaxial breathing circuit may include an outer conduit 11 and an inner conduit 10. Preferably, for heat transfer reasons, the inner conduit 10 carries the inspiratory flow in the space 12 there within. The expiratory flow is carried in the space 13 between the inner conduit 10 and the outer conduit 11, and a doubled back heated wick 100 is provided in the expiratory flow space. The airflow configuration is indicated by arrows 20, 19 respectively in FIG. 5.

The inner conduit 10 is formed having one or more longitudinal strips 2, 3 of breathable membrane in the wall 1 thereof, as has previously been described with reference to FIGS. 1A-1D, 2 and 3. Thus humidity in the expiratory flow space 13 may pass through the sections 2, 3 of breathable membrane to humidify the inspiratory flow in inspiratory flow space 12.

The breathable membrane works on relative partial pressures of water vapour so, with the flows in a counter flow arrangement substantial passive humidification of the inspiratory flow can be achieved.

Referring to FIG. 5 a circuit configuration including the coaxial conduit depicted in FIG. 4 is represented, but with a heated wick 100 disposed in both of the inspiratory and expiratory flow paths (for example doubling back at the patient end connector 15). In this circuit the conduit has a patient end connector 15 and a ventilator end connector 16 having inspiratory port 17 and an expiratory port 18. The inspiratory 20 and expiratory 19 counter flows are indicated.

So in its broadest form the invention is a conduit for a breathing circuit which includes a heater associated, at least in part with a hydrophilic layer to attract liquid water or condensate to itself. The purpose of the heater is to evaporate any condensed liquid collecting in the conduit. The heated wick is not a humidifier and so no liquid is supplied directly to the hydrophilic material from outside said conduit. The heated wick reduces the risk of collected water being passed to the patient and causing choking fits or discomfit. It also improves the predictability of the humidity levels in the gases passed to the patient. It is preferred that the heated wick lies freely in the conduit to settle at low points in the conduit where condensation may collect.

Where the conduit in question is an expiratory conduit, or at least where the heated wick is located in an expiratory flow path of a breathing circuit, then the heated wick will have additional benefits where the conduit has at least of portion of its wall formed from breathable material for passive dehumidification of the expired gases. Because the breathable material will pass only vapour, evaporation of any condensed liquid within the conduit will allow that liquid to subsequently be passed.

Another aspect to the invention is the construction of the heated wick, which is preferably an elongate heating element covered with an inner hydrophobic insulating layer co-extruded with an outer hydrophilic layer.

It will be appreciated that the concepts encapsulated by the described and illustrated embodiments are not restricted to being combined only as described. For example the heated wick described with reference to FIGS. 6 and 7 may be used in the coaxial conduit of FIGS. 4 and 5 or the separate limbed conduit as in FIG. 6. Similarly the conduit incorporating the breathable membrane, whether it be the inner conduit of the coaxial configuration shown in FIGS. 4 and 5 or the stand alone expiratory limb of FIG. 6, may be formed as a co-extrusion as in FIGS. 1A-1D and 3 or as an extruded tape as in FIG. 8 and with the breathable membrane being of a number of alternate materials. While some embodiments have been described as preferred and convey particular advantages over other embodiments many other combinations may prove commercially useful.

What is claimed is:

1. A conduit for a breathing circuit, the conduit comprising:
   an enclosing wall having a first end and a second end, the enclosing wall comprising an extrusion comprising a breathable material that allows passage of water vapor through the enclosing wall without allowing passage of liquid water through the enclosing wall; and
   a heater positioned within the conduit, the heater comprising at least one elongate heating element, the at least one elongate heating element being at least partially covered with an outer hydrophilic layer, the outer hydrophilic layer being constructed of a water-resistant material, and the outer hydrophilic layer attracting water into spaces and/or voids on an outer surface of the outer hydrophilic layer through capillary action, the heater being positioned freely within the conduit such that at least a part of the heater is configured to settle at a low point in the conduit.

2. The conduit of claim 1, wherein the at least one heating element comprises heater wire strands, the heater wire strands being coated in an electrical insulating material, and the heater wire strands being formed into a braided mesh tube that defines the outer hydrophilic layer.

3. The conduit of claim 2, wherein the braided mesh tube forms a heated wick that can attract water through capillary action.

4. The conduit of claim 1, wherein the at least one elongate heating element comprises at least one positive wire and at least one negative wire, the at least one positive wire and the at least one negative wire being arranged co-axially, each of the at least one positive wire and the at least one negative wire being surrounded by an electrical insulating layer, and the at least one positive wire and the at least one negative wire being surrounded by an outer water-attracting braid that defines the outer hydrophilic layer.

5. The conduit of claim 4, wherein the outer water-attracting braid defines the spaces and/or voids on the outer surface of the outer hydrophilic layer.

6. The conduit of claim 1, wherein the water-resistant material is polyethylene terephthalate (PET).

7. The conduit of claim 1, wherein the water-resistant material is polyethylene or polypropylene.

8. The conduit of claim 1, wherein the outer hydrophilic layer is formed from a partially foamed plastic layer.

9. The conduit of claim 1, wherein the outer hydrophilic layer is formed by sintering.

10. The conduit of claim 1, wherein the heater comprises a plurality of elongate heating elements.

11. The conduit of claim 1, wherein the at least one elongate heating element is imbedded in the outer hydrophilic layer.

12. The conduit of claim 1, wherein the at least one elongate heating element is covered with an inner insulating layer.

13. The conduit of claim 1, wherein the outer layer comprises grooves and/or fins, the grooves and/or fins being configured to facilitate capillary action.

14. The conduit of claim 13, wherein the grooves are axial, annular, helical, or knurled in a crisscross configuration.

* * * * *